United States Patent
Knappe et al.

(10) Patent No.: US 10,617,628 B2
(45) Date of Patent: Apr. 14, 2020

(54) COMPOSITIONS FOR KERATIN-CONTAINING FIBERS, COMPRISING AT LEAST ONE SPECIFIC UNCROSSLINKED ANIONIC POLYMER AND AT LEAST ONE FURTHER SPECIFIC UNCROSSLINKED CATIONIC POLYMER

(71) Applicant: Henkel AG & Co. KGaA, Duesseldorf (DE)

(72) Inventors: Thorsten Knappe, Schenefeld (DE); Marie Meisel, Hemslingen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 602 days.

(21) Appl. No.: 15/321,026

(22) PCT Filed: May 13, 2015

(86) PCT No.: PCT/EP2015/060544
§ 371 (c)(1),
(2) Date: Dec. 21, 2016

(87) PCT Pub. No.: WO2015/197259
PCT Pub. Date: Dec. 30, 2015

(65) Prior Publication Data
US 2017/0135945 A1    May 18, 2017

(30) Foreign Application Priority Data

Jun. 23, 2014 (DE) .......... 10 2014 211 975

(51) Int. Cl.
| | | |
|---|---|---|
| A61Q 5/06 | (2006.01) | |
| A61K 8/92 | (2006.01) | |
| A61K 8/81 | (2006.01) | |
| A61K 8/04 | (2006.01) | |
| A61K 8/31 | (2006.01) | |
| A61K 8/891 | (2006.01) | |

(52) U.S. Cl.
CPC ............. *A61K 8/922* (2013.01); *A61K 8/046* (2013.01); *A61K 8/31* (2013.01); *A61K 8/8105* (2013.01); *A61K 8/8147* (2013.01); *A61K 8/8152* (2013.01); *A61K 8/8176* (2013.01); *A61K 8/8182* (2013.01); *A61K 8/891* (2013.01); *A61Q 5/06* (2013.01); *A61K 2800/548* (2013.01); *A61K 2800/5424* (2013.01); *A61K 2800/5426* (2013.01); *A61K 2800/594* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 8,741,273 B2 | 6/2014 | Knappe et al. | |
| 2009/0226390 A1* | 9/2009 | Birkel ................... | A61K 8/042 424/70.13 |

FOREIGN PATENT DOCUMENTS

| | | |
|---|---|---|
| EP | 2090281 A1 | 8/2009 |
| EP | 2468238 A2 | 6/2012 |

OTHER PUBLICATIONS

EPO, International Search Report and Written Opinion issued in International Application No. PCT/EP2015/060544, dated Jul. 21, 2015.
EPO, International Preliminary Report on Patentability issued in International Application No. PCT/EP2015/060544, dated Dec. 27, 2016.
Database GNPD [Online]. Mintel. "Extra Strong Hold Styling Gel," Jan. 1, 2011. Database Accession No. 1464289.
Database GNPD [Online]. Mintel. "Ultra Styling Gel," Dec. 1, 2009. Database Accesssion No. 1239973.
Database GNPD [Online]. Mintel. "Ultra Styling Hair Gel," Jun. 1, 2009. Database Accesssion No. 1122220.
Carnegie Mellon University—"Polymer Architecture"—Gelfand Center, 2019 https://www.cmu.edu/gelfand/education/k12-teachers/polymers/polymer-architecture/index.html.

* cited by examiner

*Primary Examiner* — Jyothsna A Venkat
(74) *Attorney, Agent, or Firm* — Lorenz & Kopf, LLP

(57) ABSTRACT

Cosmetic compositions for temporarily deforming keratinic fibers, cosmetic products, and methods for temporarily deforming keratinic fibers are provided herein. In one embodiment, a cosmetic composition for temporarily deforming keratinic fibers includes at least one uncrosslinked anionic polymer, at least one uncrosslinked cationic polymer, and water in a total amount of from about 80 to about 98% by weight, in relation to the total weight of the cosmetic composition.

5 Claims, No Drawings

COMPOSITIONS FOR KERATIN-CONTAINING FIBERS, COMPRISING AT LEAST ONE SPECIFIC UNCROSSLINKED ANIONIC POLYMER AND AT LEAST ONE FURTHER SPECIFIC UNCROSSLINKED CATIONIC POLYMER

CROSS-REFERENCE TO RELATED APPLICATION

This application is a U.S. National-Stage entry under 35 U.S.C. § 371 based on International Application No. PCT/EP2015/060544, filed May 13, 2015, which was published under PCT Article 21(2) and which claims priority to German Application No. 10 2014 211 975.8, filed Jun. 23, 2014, which are all hereby incorporated in their entirety by reference.

TECHNICAL FIELD

The application relates to the specialist technical field of temporary forming of keratin-containing fibers, in particular human hair. The subject of the application is constituted by cosmetic compositions containing at least one specific uncrosslinked anionic polymer and at least one specific uncrosslinked cationic polymer, and also by cosmetic products, comprising a dispensing device with spray valve and also the aforementioned cosmetic compositions. A further subject of the present application is additionally the use of these cosmetic compositions and products for the temporary forming of keratin-containing fibers, and also corresponding methods of use.

BACKGROUND

A nice-looking hairstyle is nowadays generally regarded as an essential part of a well-groomed appearance. Time and time again, based on current fashion trends, hairstyles that can be constructed with many types of hair using only firming active ingredients or that stay in place for a relatively long period of time up to several days are considered chic. Hair treatment compositions that permanently or temporarily shape the hair therefore play an important role. Whereas, in the case of permanent forming, the chemical structure of the keratin-containing fibers is modified by reduction and oxidation, no such modification of the chemical structure takes place in the case of temporary forming. Corresponding compositions for temporary deformation usually contain synthetic polymers and/or waxes as firming active ingredient.

The most important property of a composition for temporarily deforming keratinic fibers, also referred to hereinafter as styling compositions, lies in providing the treated fibers with the greatest possible hold in the newly modeled form—i.e. a form impressed on the fibers. If the keratinic fibers are human hair, reference is also made to a strong hairstyle hold or to a high holding power of the styling composition. The hold of a hairstyle is determined fundamentally by the type and quantity of the used firming active ingredients, however the further constituents of the styling composition and also the application form can also have an effect.

In addition to a high holding power, styling compositions must also satisfy a wide range of further requirements. These can be divided roughly into properties on the hair, properties of the respective formulation, for example properties of sprayed aerosol or non-aerosol, and properties that concern the handling of the styling composition, wherein the properties on the hair are attributed particular importance. In particular, moisture resistance, low stickiness, and a balanced conditioning effect can be cited. Furthermore, a styling composition should be universally usable for all hair types where possible and should be mild on the hair and skin.

In order to satisfy the different requirements, a multiplicity of synthetic polymers which are used in styling compositions have been developed in the prior art as firming active ingredients. These polymers can be divided into cationic, anionic, non-ionic and amphoteric firming polymers. When applied to the hair, the polymers ideally provide a polymer film, which on the one hand gives the hairstyle a stronger hold, but on the other hand is sufficiently flexible so as not to break under load. If the polymer film is too brittle, this results in the formation of what are known as film flakes or residues, which come loose as the hair moves and give the impression that the user of the corresponding styling composition has dandruff. Similar problems are encountered when wax is used as a firming active ingredient in the styling composition.

Compositions for assisting the temporary forming of keratin-containing fibers can be produced for example as a hairspray, hair wax, hair gel, or hair mousse. In particular, the application in the form of a spray by means of a spraying device is highly popular. However, the application by means of a spraying device requires additional measures, depending on the nature of the styling composition. By way of example, an application by spraying of thickened hair gels in the prior art was previously possible only with use of a specific combination of thickening agent and styling polymer, since only in this way could a sufficient nebulization of the hair gel be ensured by means of the spraying application. The combination of a carbomer and PVP/VA styling polymers used in the prior art can indeed provide sufficient nebulization, but does not provide satisfactory prolonged hold or volume effect and therefore fails to satisfy consumer needs.

BRIEF SUMMARY

Cosmetic compositions for temporarily deforming keratinic fibers, cosmetic products, and methods for temporarily deforming keratinic fibers are provided herein. In one embodiment, a cosmetic composition for temporarily deforming keratinic fibers includes at least one uncrosslinked anionic polymer, at least one uncrosslinked cationic polymer, and water in a total amount of from about 80 to about 98% by weight, in relation to the total weight of the cosmetic composition.

In another embodiment, a cosmetic product includes a dispensing device with spray valve. The cosmetic product further includes a cosmetic composition disposed in the dispensing device. The cosmetic composition includes at least one uncrosslinked anionic polymer, at least one uncrosslinked cationic polymer, and water in a total amount of from about 80 to about 98% by weight, in relation to the total weight of the cosmetic composition. The cosmetic product further includes a propellant in a total amount of from 0 to about 95% by weight, in relation to the total weight of the cosmetic composition disposed in the dispensing device.

In another embodiment, a method for temporarily deforming keratinic fibers includes the step of providing a cosmetic composition. The cosmetic composition includes at least one uncrosslinked anionic polymer, at least one uncrosslinked cationic polymer, and water in a total amount of from about 80 to about 98% by weight, in relation to the total weight of the cosmetic composition. The method further includes the step of applying the cosmetic composition onto the keratinic fibers. The method further includes the step of distributing the applied cosmetic composition over the keratinic fibers and deforming the keratinic fibers into the desired form.

DETAILED DESCRIPTION

The following detailed description is merely exemplary in nature and is not intended to limit the disclosure or the application and uses of the disclosure. Furthermore, there is not intention to be bound by any theory presented in the preceding background or the following detailed description.

The object of the present disclosure was therefore to provide compositions for temporarily deforming keratin-containing fibers, which compositions are provided in the form of a thickened gel and can be applied in an effective manner as a targeted spray mist to the keratin-containing fibers. The compositions for temporarily deforming keratin-containing fibers should also have a high holding power, in particular prolonged holding power, and a high volume effect.

It has now surprisingly been found that a combination of a specific uncrosslinked anionic polymer with a specific uncrosslinked cationic polymer leads to thickened styling compositions which, in spite of the thickened state, can be nebulized in an excellent manner and therefore can be applied as a fine spray mist to the keratinic fibers. The aforementioned combination of specific polymers also results in a high prolonged hold and a good volume effect, i.e. a greater volume of the keratinic fibers treated with the cosmetic compositions as contemplated herein.

A first subject of the present disclosure is thus a cosmetic composition for temporarily deforming keratinic fibers, containing a) at least one uncrosslinked anionic polymer, comprising at least one structural unit of formula (I) and at least one structural unit of formula (II) and at least one structural unit of formula (III)

(I)

(II)

(III)

in which

R and $R^2$, independently of one another, stand for a hydrogen atom or a $C_1$-$C_4$ alkyl chain, $R^1$ stands for a branched or unbranched, saturated or unsaturated $C_1$-$C_{12}$ alkyl chain, $R^3$ stands for a branched or unbranched, saturated or unsaturated $C_8$-$C_{20}$ alkyl chain, $R^4$ stands for a $C_1$-$C_4$ alkyl chain, A stands for a group $*-(CH_2CH_2O)_x-*$ or $*-(CH_2CHMeO)_y-*$ or $*-(CH_2CH_2O)_x-(CH_2CHMeO)_y-*$, in which x and y, independently of one another, stand for integers from 5 to 35, $X^+$ stands for a physiologically acceptable cation, b) at least one uncrosslinked cationic polymer, comprising at least one structural unit of formula (IV) and at least one structural unit of formula (V) and at least one structural unit of formula (VI) and at least one structural unit of formula (VII)

(IV)

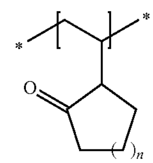

(V)

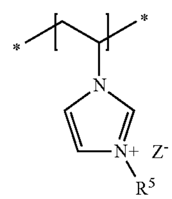

(VI)

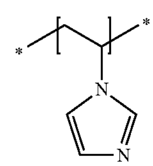

(VII)

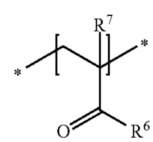

in which n stands for 1, 2 or 3 methylene unit(s), $R^5$ stands for a hydrogen atom, a $C_1$-$C_{30}$ alkyl group, a $C_1$-$C_4$ alkyl group, a $C_2$-$C_6$ alkenyl group, or a $C_2$-$C_6$ hydroxylalkyl group, $R^6$ stands for a group $O^-X^+$, in which $X^+$ is a physiologically acceptable cation, or stands for an $NH_2$ group, $R^7$ stands for a hydrogen atom or a $C_1$-$C_4$ alkyl chain, $Z^-$ stands for a physiologically acceptable anion, and c) water in a total amount of from about 80 to about 98% by weight, in relation to the total weight of the cosmetic composition.

Due to the combination of a specific anionic uncrosslinked polymer with a specific cationic uncrosslinked polymer, thickened, in particular gel-like cosmetic compositions are obtained, which, in spite of the gel-like consistency, can be nebulized in an excellent manner and therefore can be applied as a fine spray mist to keratinic fibers, in particular human hair. Due to the fine nebulization, a uniform application of the cosmetic compositions as contemplated herein to the keratinic fibers is ensured, and a blocking of the spray valve of the dispensing device is avoided. In addition, the aforementioned combination of specific uncrosslinked anionic and cationic polymers results in a high prolonged hold and a high volume effect.

In accordance with the above formulas and all subsequent formulas, a chemical bond characterized by the symbol "*" stands for a free valence of the corresponding structure fragment. Here, a "free valence" is understood to mean the number of atomic bonds emanating from the corresponding structure fragment in the position characterized by the symbol "*". Within the scope of the present disclosure, an atomic bond preferably emanates from each of the positions of the structure fragments characterized by the symbol "*" to further structure fragments.

The term "keratin-containing fibers" is understood in principle to mean all animal hair, for example wool, horsehair, angora hair, fur, feathers and products or textiles produced therefrom. The keratinic fibers, however, are preferably human hair.

Within the scope of the present disclosure, the term "anionic polymers" is understood to mean polymers which, in a protic solvent, carry at least one structural unit having permanently anionic groups, wherein the anionic groups must be compensated for by counterions whilst maintaining electroneutrality. Anionic groups, in accordance with the disclosure, include in particular carboxyl and sulfonic acid groups. In this context, the term "cationic polymers" is understood to mean polymers which, in a protic solvent under standard conditions, carry at least one structural unit having permanently cationic groups, wherein the cationic groups also have to be compensated for by counterions whilst maintaining the electroneutrality. Permanently cationized groups are understood to mean groups which form a quaternary ammonium compound. Quaternary ammonium compounds are usually produced by reacting tertiary amines with alkylating agents, such as methyl chloride, benzyl chloride, dimethyl sulfate, dodecyl bromide, but also ethylene oxide. Depending on the used tertiary amine, the following groups in particular are known: alkyl ammonium compounds, alkenyl ammonium compounds, imidazolinium compounds, and pyridinium compounds. Polymers which contain exclusively cationic groups in the form of protonated amines do not fall within the scope of the present disclosure of used "cationic polymers".

The term "uncrosslinked" within the scope of the present disclosure is understood to mean polymers which have no linking of the polymer chains by a direct covalent bonding of the polymer chains or by bridging molecule fragments bonded covalently to the polymer chains. Uncrosslinked polymers in the sense of the present disclosure therefore do not have a network formed by covalent chemical bonds.

Furthermore, the term "sprayable cosmetic compositions" or "nebulizable cosmetic compositions" within the scope of the present disclosure is understood to mean cosmetic compositions which can be sprayed with use of spraying devices, in particular aerosol containers or non-aerosol containers having spray valves, and which in so doing do not block these valves. In accordance with the disclosure, the nebulization or the spraying of these cosmetic compositions by means of spray devices preferably leads to a fine and targeted spray mist.

In addition, the term "physiologically acceptable cations" is understood to mean cations which are not poisonous or not toxic or which are safe for the organism, in particular the human and the animal organism.

In addition, the term "fatty acid" as used within the scope of the present disclosure is understood to mean aliphatic carboxylic acids which comprise unbranched or branched carbon groups having 4 to 40 carbon atoms. The fatty acids used within the scope of the present disclosure can be either naturally occurring or also synthetically produced fatty acids. The fatty acids can also be monounsaturated or polyunsaturated.

Lastly, the term "fatty alcohol" within the scope of the present disclosure is understood to mean aliphatic, monovalent, primary alcohols which comprise unbranched or branched hydrocarbon groups having 4 to 40 carbon atoms. The fatty alcohols used within the scope of the disclosure can also be single or multiple.

As first essential constituent a), the cosmetic composition as contemplated herein contains at least one specific uncrosslinked anionic polymer on the basis of the structural units of formulas (I) to (III). In the structural units of formulas (I) and (II), the groups R, $R^2$ and $R^4$ stand for ($C_1$ to $C_4$) alkyl groups. Examples of these are methyl, ethyl, propyl, isopropyl, butyl, sec-butyl, isobutyl and also tert-butyl groups. Examples of ($C_8$ to $C_{20}$) alkyl groups as contemplated herein of the group $R^3$ in the structural unit of formula (III) are octyl (capryl), decyl (caprinyl), dodecyl (lauryl), tetradecyl (myristyl), hexadecyl (cetyl), octdecyl (stearyl) and also eicosyl (arachyl) groups.

In accordance with a first embodiment of the present disclosure, the groups R and $R^2$ in the structural units of the formulas (I) and (II) each stand, independently of one another, for a hydrogen atom or a methyl group, and the group $R^4$ in the structural unit of formula (III) stands for a methyl group.

Within the scope of the present disclosure, provision can be made additionally so that the group $R^1$ in the structural unit of formula (I) stands for a ($C_2$ to $C_4$) alkyl group, in particular for an ethyl group.

With regard to the thickening and the simultaneously good nebulizability of the cosmetic compositions as contemplated herein, it has proven to be advantageous if, in the structural unit of formula (III), the group A stands for a group *—$(CH_2CH_2O)_x$—*, in which x stands for integers from 5 to 35, preferably from 10 to 30, in particular from 15 to 25.

Particularly good results are obtained within the scope of the present disclosure when, in the structural unit of formula (III), the group $R^3$ stands for a saturated and linear $C_{10}$-$C_{20}$ alkyl group, preferably for a saturated and linear $C_{12}$-$C_{20}$ alkyl group, more preferably for a saturated and linear $C_{14}$-$C_{20}$ alkyl group, in particular for a saturated and linear $C_{16}$-$C_{20}$ alkyl group.

It is preferred in accordance with the disclosure when, in the structural unit of formula (I), $X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom. Cationic organic compounds can be obtained for example by protonation of primary, secondary, or tertiary organic amines with an acid, or by permanent quaternization of said organic amines. Examples of cationic organic ammonium compounds that are suitable within the scope of the present disclosure are, for example, 2-ammonioethanol and 2-trimethylammonioethanol.

Within the context of the present disclosure it is preferred when the cosmetic composition contains at least one uncrosslinked anionic polymer which comprises at least one structural unit of formula (I) and at least one structural unit of formula (II) and at least one structural unit of formula (III)

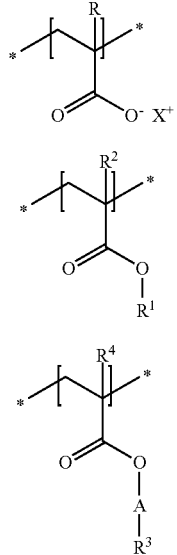

in which

R and $R^2$, independently of one another, stand for a hydrogen atom or a methyl group, $R^1$ stands for a $C_2$-$C_4$ alkyl chain, in particular an ethyl group, $R^3$ stands for a saturated and linear $C_{16}$-$C_{20}$ alkyl group, $R^4$ stands for a methyl group, A stands for a group *—$(CH_2CH_2O)_x$—*, in which x stands for integers from 15 to 25, and $X^+$ stands for metal cations of the physiologically acceptable metals from the groups Ia, Ib, IIa, IIb, IIb, IIIb, VIa or VIII of the Periodic Table of Elements, ammonium ions, and also cationic organic compounds with quaternized nitrogen atom.

In accordance with a particularly preferred embodiment of the present disclosure, the cosmetic composition as contemplated herein contains at least one uncrosslinked anionic polymer which comprises at least one structural unit of formula (Ia) and at least one structural unit of formula (Ib) and at least one structural unit of formula (IIa) and at least one structural unit of formula (IIb) and at least one structural unit of formula (III)

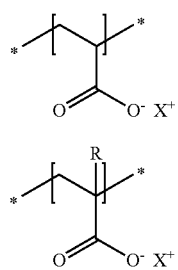

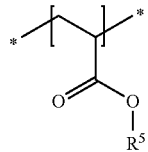

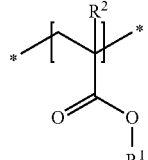

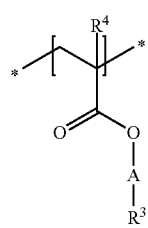

in which

R, $R^2$ and $R^4$, independently of one another, stand for a methyl group, $R^1$ and $R^5$, independently of one another, stand for a $C_2$-$C_4$ alkyl chain, in particular an ethyl group, $R^3$ stands for a saturated and linear $C_{16}$-$C_{20}$ alkyl group, $R^4$ stands for a methyl group, A stands for a group *—$(CH_2CH_2O)_x$—*, in which x stands for integers from 15 to 25, and $X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom. The use of these specific uncrosslinked anionic polymers leads to thickened, in particular gel-like cosmetic compositions which, in spite of the thickened state, can be sprayed in an excellent manner and can be distributed as a fine spray mist onto the keratinic fibers, in particular human hair. In addition, there is no blocking of the spray valves of the dispensing devices when the cosmetic compositions as contemplated herein thickened with these specific polymers are sprayed.

A very particularly preferred uncrosslinked anionic polymer within the scope of this embodiment is a polymer with the INCI name Acrylates/Steareth-20 Methacrylate Copolymer. This polymer contains functionalized methacrylate monomers which contain 20 ethylene oxide units (A in structural unit of formula (III) stands for a group *—$(CH_2CH_2O)_x$—* with x=20) and are etherified with stearyl alcohol ($R^3$ according to structural unit of formula (III)=Stearyl). Such polymers are sold for example under the trade name Aculyn® 22 by the company Rohm & Haas in the form of a about 29.5 to about 30.5% dispersion in water.

Preferred cosmetic compositions as contemplated herein contain the at least one uncrosslinked anionic polymer a) in a total amount of from about 0.05 to about 2% by weight, preferably from about 0.1 to about 1.5% by weight, in particular from about 0.2 to about 1% by weight, in relation to the total weight of the cosmetic composition. The use of the aforementioned amounts of the specific uncrosslinked anionic polymer a) results on the one hand in a sufficient thickening of the cosmetic composition as contemplated herein, such that the cosmetic compositions as contemplated herein, in spite of the gel-like consistency, have excellent nebulization properties and can be sprayed as a fine spray mist, without blocking the spray valves of the dispensing devices.

As second essential constituent b), the cosmetic composition as contemplated herein contains at least one specific uncrosslinked cationic polymer based on the structural units of formulas (IV) to (VII). The use of this cationic polymer results in a high prolonged hold and also in an improved volume of the keratinic fibers deformed using the cosmetic compositions as contemplated herein.

In accordance with a preferred embodiment of the present disclosure, n in the structural unit of formula (IV) stands for a methylene unit.

In addition, it is preferred in accordance with the disclosure when, in the structural unit of formula (V), the group $R^5$ stands for a methyl group and $Z^-$ stands for methosulfate.

Within the scope of the present disclosure, it is additionally preferred when, in the structural unit of formula (VII), the group $R^6$ stands for an $NH_2$ group and the group $R^7$ stands for a methyl group.

Within the scope of the present disclosure, it is therefore very particularly preferred when the cosmetic composition contains at least one uncrosslinked cationic polymer comprising at least one structural unit of formula (IV) and at least one structural unit of formula (V) and at least one structural unit of formula (VI) and at least one structural unit of formula (VII)

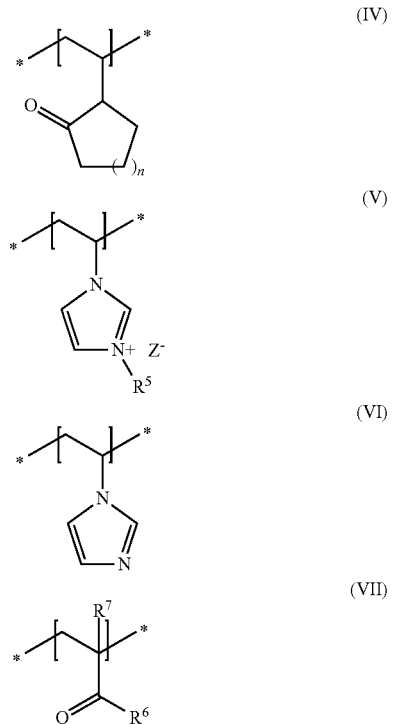

in which
n stands for a methylene unit,
$R^5$ stands for a methyl group,
$R^6$ stands for an $NH_2$ group,
$R^7$ stands for a methyl group, and $Z^-$ stands for methosulfate. The use of these specific uncrosslinked cationic polymers leads to a good prolonged hold and also to an increased volume of the keratinic fibers treated with the cosmetic compositions as contemplated herein.

It is particularly preferred within the scope of the present disclosure when the uncrosslinked cationic polymer consists to an extent of at least 70% by weight, preferably at least 80% by weight, preferably at least 90% by weight, in particular at least 95% by weight, in relation to the total weight of the uncrosslinked cationic polymer, of structural units of formulas (IV), (V), (VI) and (VII).

An uncrosslinked cationic polymer that is very particularly preferred in accordance with the disclosure is formed from N-vinylpyrrolidone (formula IV), 3-methyl-1-vinylimidazolium methyl sulfate (formula V), N-vinylimidazole (formula VI) and methacrylic acid amide (formula VII). Such polymers are named in accordance with INCI nomenclature as Polyquaternium-68 and are obtainable for example from the company BASF under the trade names Luviquat® Supreme as 19 to 21% dispersion in water.

Preferred cosmetic compositions as contemplated herein contain the at least one uncrosslinked cationic polymer b) in a total amount of from about 0.1 to about 5% by weight, preferably from about 0.2 to about 5% by weight, preferably from about 0.3 to about 3% by weight, in particular from about 0.5 to about 2% by weight, in relation to the total weight of the cosmetic composition. The use of the aforementioned quantities of the specific uncrosslinked cationic polymer b) results on the one hand in an improved prolonged hold. On the other hand, the use of the specific polymer results in an improved volume of the keratinic fibers treated using the cosmetic compositions as contemplated herein and also in an extended longevity of this volume.

Particularly preferred cosmetic compositions as contemplated herein are therefore those which comprise
a) at least one uncrosslinked anionic polymer, comprising at least one structural unit of formula (I) and at least one structural unit of formula (II) and at least one structural unit of formula (III)

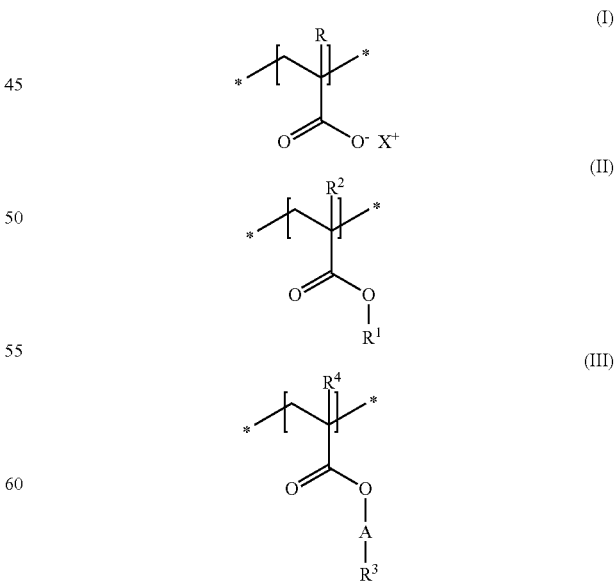

in which
R and $R^2$, independently of one another, stand for a hydrogen atom or a methyl group, $R^1$ stands for a $C_2$-$C_4$ alkyl chain, in particular an ethyl group,
$R^3$ stands for a saturated and linear $C_{16}$-$C_{20}$ alkyl group,
$R^4$ stands for a methyl group,
A stands for a group *—$(CH_2CH_2O)_x$—*, in which x stands for integers from 15 to 25, and
$X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, and b) at least one uncrosslinked cationic polymer, comprising at least one structural unit of formula (IV) and at least one structural unit of formula (V) and at least one structural unit of formula (VI) and at least one structural unit of formula (VII)

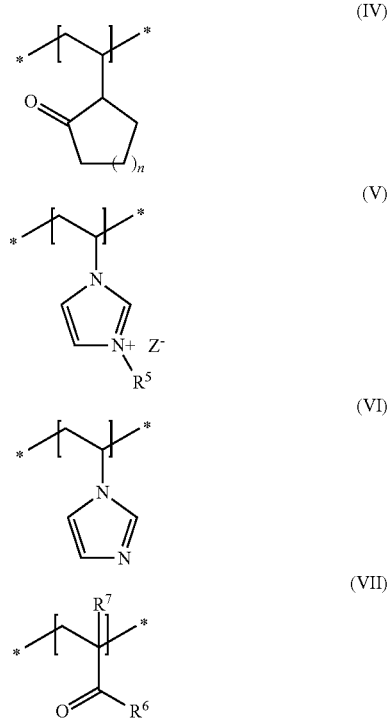

in which
n stands for a methylene unit,
$R^5$ stands for a methyl group,
$R^6$ stands for an $NH_2$ group,
$R^7$ stands for a methyl group, and
$Z^-$ stands for methosulfate. The use of the aforementioned specific polymer combination is particularly advantageous in view of a sufficient thickening alongside excellent nebulizability as well as a high prolonged hold and volume effect. The aforementioned polymer combination of a specific uncrosslinked anionic polymer as thickening agent and a specific uncrosslinked cationic polymer having a high holding power results in cosmetic compositions as contemplated herein which, in spite of their gel-like consistency, demonstrate excellent nebulization properties without blocking the spray valves of dispensing devices and additionally have a high holding power and also a high volume effect.

Particularly good results in respect of excellent nebulizability and also a high prolonged hold and a high volume effect are obtained when the cosmetic composition has a ratio by weight of the total amount of the at least one uncrosslinked anionic polymer a) to the total amount of the at least one uncrosslinked cationic polymer b) of from about 10:1 to about 1:30, preferably from about 5:1 to about 1:30, preferably from about 1:1 to about 1:30, more preferably from about 1:1.5 to about 1:20, in particular from about 1:2 to about 1:15.

In particular, in respect of the sprayability of the cosmetic compositions as contemplated herein, it is advantageous when the cosmetic composition contains water in a total amount of from about 82 to about 98% by weight, preferably from about 85 to about 98% by weight, preferably from about 87 to about 98% by weight, more preferably from about 89 to about 98% by weight, in particular from about 91 to about 98%, in relation to the total weight of the cosmetic composition.

Within the scope of this embodiment, however, provision can also be made so that the cosmetic composition as contemplated herein also contains at least one solvent which is liquid at 25° C. and 1013 mbar and which is different from water in a total amount of from about 1% by weight to about 50% by weight, preferably from about 5% by weight to about 40% by weight, in particular from about 10% by weight to about 30% by weight, in relation to the total weight of the cosmetic composition.

It can be preferred in accordance with the disclosure when at least one ($C_2$ to $C_6$) alkyl alcohol having at least one hydroxy group is used as additional solvent of the composition as contemplated herein. Within the scope of a particularly preferred embodiment of the composition as contemplated herein, the composition contains, as additional solvent, at least one alcohol comprising 2 to 6 carbon atoms and 1 to 3 hydroxyl groups.

The solvent different from water is preferably selected from at least one compound of the group formed from ethanol, ethylene glycol, isopropanol, 1,2-propylene glycol, 1,3-propylene glycol, glycerol, n-butanol, 1,3-butylene glycol. A very particularly preferred solvent is ethanol.

Further particularly preferred solvents are polyethylene glycol and/or propylene glycol.

In particular, the addition of polyethylene glycol and/or propylene glycol increases the flexibility of the polymer film formed with application of the cosmetic composition as contemplated herein. If a flexible hold is thus desired, the cosmetic compositions as contemplated herein preferably contain a total amount of from about 0.01 to about 30% by weight of polyethylene glycol and/or propylene glycol, in relation to the total weight of the cosmetic composition.

It has also proven to be advantageous in respect of the sprayability of cosmetic compositions as contemplated herein when the cosmetic composition contains less than 0.1% by weight, preferably less than 0.05% by weight, preferably less than 0.01% by weight, in particular 0% by weight, in relation to the total weight of the cosmetic composition, of crosslinked polymers. The term “crosslinked” or “crosslinking” is to be understood within the sense of the disclosure to mean the linking of polymer chains by covalent chemical bonds, resulting in the formation of a network. This covalent linking of the polymer chains can be provided by means of direct covalent bonding or by a molecule fragment bridging the polymer chains. The molecule fragment bonds to the polymer chains bridged by the molecule fragment, in each case by means of covalent chemical bonding.

Within the scope of the present disclosure, provision can be made so that the cosmetic composition also contains at least one alkanolamine, in particular 2-amino-2-methyl-1-propanol.

The prolonged hold of the cosmetic composition as contemplated herein can be further increased when the cosmetic composition additionally contains at least one film-forming and/or firming polymer. Film-forming or firming polymers contribute, by the formation of a film, to the hold of the impressed form of the collective body of fibers, for example the hairstyle as a whole. The film formation can be provided at quite specific points and may connect only some fibers to one another. Film-forming or firming polymers are to be understood to mean those polymers which, as they dry, leave behind a continuous film on the skin, the hair, or the nails. Film formers of this type can be used in the different cosmetic products, such as face masks, make-up, hair setting agents, hairsprays, hair gels, hair waxes, hair masks, shampoos, or nail varnishes. In particular, polymers which have a solubility in water or water/alcohol mixtures sufficient to be present in fully dissolved form in the cosmetic compositions as contemplated herein are preferred. The film-forming polymers can be of synthetic or natural origin. Film-forming polymers are also understood to be polymers which, when used in about 0.01 to about 20% by weight aqueous, alcoholic or aqueous-alcoholic solution, are capable of being deposited on the hair in a transparent polymer film.

In this regard, provision can be made in particular in accordance with the disclosure so that the additional at least one film-forming and/or firming polymer selected from copolymers or polyvinylpyrrolidone and vinyl acetate. In particular, polyvinylpyrrolidone/vinyl acetate copolymers having a molar ratio of polyvinylpyrrolidone to vinyl acetate of 70 to 30, 60 to 40, 50 to 50, or 30 to 70 can be used within the scope of the present disclosure. PVP/VA copolymers of this type having a molar ratio of polyvinylpyrrolidone to vinyl acetate of 70 to 30 are obtainable for example under the trade names PVP/VA E-735, PVP/VA I-735 and PVP/VA W-735 as 50% dispersion in ethanol, isopropanol or water from the company Ashland. PVP/VA copolymers having a molar ratio of polyvinylpyrrolidone to vinyl acetate of 60 to 40 are obtainable for example under the trade names PVP/VA E-635 and PVP/VA W-635 as 50% dispersion in ethanol, isopropanol or water from the company Ashland. PVP/VA copolymers having a molar ratio of polyvinylpyrrolidone to vinyl acetate of 50 to 50 as 50% dispersion in ethanol or isopropanol are obtainable from the company Ashland under the trade names PVP/VA E-535 and PVP/VA I-535. A PVP/VA copolymer having a molar ratio of polyvinylpyrrolidone to vinyl acetate of 30 to 70 is sold for example under the trade name PVP/VA I-335 as 50% dispersion in isopropanol by the company Ashland.

Besides the copolymers of polyvinylpyrrolidone and vinyl acetate, the cosmetic compositions as contemplated herein can contain further film-forming and/or firming polymers selected from the group of non-ionic film-forming and/or firming polymers, amphoteric film-forming and/or firming polymers and also mixtures thereof.

Non-ionic polymers are understood within the scope of the present disclosure to mean polymers which have no permanently anionic or permanently cationic groups and also no anionizable or cationizable groups, such as carboxylic acid groups or amine groups. Film-forming and/or firming non-ionic polymers having at least one structural element of formula (VIII)

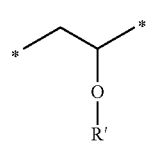

(VIII)

which are preferably suitable in accordance with the disclosure are those which, in accordance with the formula (VIII) carry a hydrogen atom, an acetyl group, or a propanoyl group, in particular an acetyl group, as R'.

The forming non-ionic polymers are in turn preferably selected from at least one polymer of the group formed from
polyvinylpyrrolidone,
copolymers of N-vinylpyrrolidone and N-vinylimidazole and methacrylamide,
copolymers of N-vinylpyrrolidone and N-vinylimidazole and acrylamide,
copolymers from N-vinylpyrrolidone with N,N-di($C_1$ to $C_4$) alkylamino to ($C_2$ to $C_4$) alkyl acyl amide,
copolymers from N-vinylpyrrolidone with N,N-di($C_1$ to $C_4$) alkylamino to ($C_2$ to $C_4$) alkyl acyl amide,
non-ionic copolymers of isobutene.

Suitable polyvinylpyrrolidones are, for example, trade products such as Luviskol® K 90 or Luviskol® K 85 from the company BASF SE. Suitable polyvinyl alcohols are sold for example under the trade names Elvanol® by Du Pont or Vinol® 523/540 by the company Air Products.

The cosmetic compositions as contemplated herein can also contain at least one film-forming and/or firming amphoteric polymer as film-forming and/or firming polymer. The term "amphoteric polymers" is understood to mean on the one hand those polymers that contain both free amino groups and free —COOH or $SO_3H$ groups in the molecule and that are capable of forming inner salts. On the other hand, zwitterionic polymers in the sense of the present disclosure also include polymers that contain quaternary ammonium groups and —COO⁻ or —$SO_3H$ groups or that contain quaternary ammonium groups and —COO⁻ or —$SO_3H$ groups in the molecule.

An example of film-forming and/or firming amphoteric polymer that can be used in accordance with the disclosure is the acrylic resin obtainable under the name Amphomer®, which constitutes a copolymer formed from tert-butylaminoethyl methacrylate, N-(1,1,3,3-tetramethylbutyl)acrylamide, and also two or more monomers from the group of acrylic acid, methacrylic acid and ($C_1$ to $C_4$) alkyl esters thereof. These polymers, in addition to the cationogenic group or positively charged group, also comprise at least one negatively charged group in the molecule and are also referred to as zwitterionic polymers.

The additional film-forming and/or forming polymers can be contained in the cosmetic compositions as contemplated herein preferably in an amount of from about 0.1% by weight to about 12.0% by weight, preferably from about 0.2% by weight to about 10.0% by weight, in particular from about 0.5% by weight to about 8.0% by weight, in each case in relation to the total weight of the cosmetic composition.

In accordance with a particularly preferred embodiment of the present disclosure, the cosmetic composition is provided in the form of a gel. The term "gel" is understood, within the scope of the present disclosure, to mean a dimensionally stable and easily deformable system formed from two components, wherein one component, in the form of the thickening agent or gel former, forms a physical, three-dimensional network, in the spaces or pores of which the second component is incorporated in the form of liquid, in particular water.

The cosmetic compositions as contemplated herein provided in accordance with this embodiment preferably have a viscosity of from about 1,000 to about 5,000 mPas, more preferably from about 1,050 to about 4,500 mPas, in particular from about 1,100 to about 4,000 mPas, in each case measured with Brookfield RVDV II+ with Heilpath, spindle 2, 5 rpm, and 20° C. Cosmetic compositions as contemplated herein which have the aforementioned viscosity have excellent nebulization properties, in spite of their thickened consistency, and do not lead to a clogging of the spray valves of the dispensing device.

Within the scope of the present disclosure it is particularly preferred when the cosmetic compositions as contemplated herein are provided as an aerosol spray or non-aerosol spray. If the cosmetic composition as contemplated herein is provided in the form of an aerosol spray, this preferably contains at least one propellant in a total amount of from about 10 to about 80% by weight, in relation to the total weight of the cosmetic composition.

Propellants that are suitable in accordance with the disclosure are selected for example from $N_2O$ dimethylether, $CO_2$ air, alkanes having 3 to 5 carbon atoms, such as propane, n-butane, iso-butane, n-pentane and iso-pentane, and mixtures thereof. Dimethylether, propane, n-butane, iso-butane and mixtures thereof are preferred. Alkanes or mixtures of the specified alkanes with dimethylether are used as sole propellant in accordance with a preferred embodiment. The present disclosure, however, also expressly comprises the co-use of propellants of the chlorofluorocarbon type, but in particular of the fluorinated hydrocarbon type.

The propellant (in particular dimethylether) is contained in the compositions as contemplated herein in the embodiment of an aerosol spray preferably in a total amount of from 30 to 60% by weight, in relation to the total weight of the cosmetic composition.

Dimethylether or mixtures of propane and butane are very particularly preferably used as sole propellant in a ratio by weight of propane to butane of from about 20 to about 80 up to about 15 to about 85. The mixtures are again preferably used in the compositions as contemplated herein in a total amount of from about 30 to about 55% by weight in relation to the total weight of the cosmetic composition. In accordance with the disclosure, "butane" is understood to mean n-butane, iso-butane and mixtures of n-butane and iso-butane. Dimethylether is most preferably used as sole propellant.

Besides the previously described specific uncrosslinked anionic and uncrosslinked cationic polymers, the cosmetic compositions as contemplated herein also contain further ingredients. The groups of these further ingredients include, in particular, cosmetically effective auxiliaries and additives, in particular additional nourishing ingredients.

By way of example, a silicone oil and/or a silicone gum can be used as nourishing ingredient. Silicone oils or silicone gums that are suitable in accordance with the disclosure are, in particular, dialkyl and alkylaryl siloxanes, such as dimethylpolysiloxane and methylphenyl polysiloxane, and also the alkoxylated, quaternized, or also anionic derivatives thereof. Cyclic and linear polydialkyl siloxanes, the alkoxylated and/or aminated derivatives thereof, dihydroxy polydimethylsiloxanes and polyphenylalkylsiloxanes, in particular PEG-12 dimethicones and PEG-14 dimethicones, are preferred.

The cosmetic composition as contemplated herein can contain, for example, at least one protein hydrolyzate and/or a derivative thereof as a nourishing ingredient of another compound class. Protein hydrolyzates are product mixtures which are obtained by acid-catalyzed, base-catalyzed or enzymatically catalyzed degradation of proteins. The term "protein hydrolyzates" is understood in accordance with the disclosure to also mean total hydrolyzates and also individual amino acids and derivatives thereof as well as mixtures of different amino acids. The molecular weight of the protein hydrolyzates usable in accordance with the disclosure lies between about 75, the molecular weight for glycine, and about 200,000 daltons, and the molecular weight is preferably about 75 to about 50,000 daltons, and in particular about 75 to about 20,000 daltons.

As nourishing ingredient, the cosmetic composition as contemplated herein can also contain at least one vitamin, a provitamin, a vitamin precursor and/or derivatives thereof. Here, vitamins, provitamins and vitamin precursors that are usually assigned to the groups A, B, C, E, F and H are preferred in accordance with the disclosure.

Similarly to the addition of glycerol and/or propylene glycol, the addition of panthenol increases the flexibility of the polymer film formed with application of the cosmetic composition as contemplated herein.

As nourishing ingredient, the cosmetic compositions as contemplated herein can also contain at least one plant extract, but also monosaccharides or oligosaccharides and/or lipids.

Oil bodies are also suitable as nourishing ingredient. Natural and synthetic cosmetic oil bodies include, for example, plant oils, liquid paraffin oils, isoparaffin oils and synthetic hydrocarbons as well as di-n-alkyl ethers having a total of between 12 and 36 C atoms, in particular 12 to 24 C atoms.

Ester oils, i.e. esters of $C_6$-$C_{30}$ fatty acids with $C_2$-$C_{30}$ fatty alcohols, preferably monoesters of the fatty acids with alcohols having 2 to 24 C atoms, such as isopropylmyristate (Rilanit® IPM), isononanoic acid C16-18 alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut fatty alcohol caprate/caprylate (Cetiol® LC), n-butyl stearate, oleyl erucate (Cetiol® J 600), isopropyl palmitate (Rilanite® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are further preferred nourishing oil bodies.

Furthermore, dicarboxylic acid esters, symmetrical, asymmetrical or cyclic esters of carbon dioxide with fatty alcohols, tri fatty acid esters of saturated and/or unsaturated linear and/or branched fatty acids with glycerol or fatty acid partial glycerides, which are understood to mean monoglycerides, diglycerides and industrial mixtures thereof, are to be understood as nourishing ingredients.

Particularly preferred embodiments (A) to (H) of the cosmetic compositions as contemplated herein will be presented hereinafter:

(A):

Cosmetic composition containing, in relation to the total weight of the cosmetic composition, a) at least one uncrosslinked anionic polymer, comprising at least one structural unit of formula (I) and at least one structural unit of formula (II) and at least one structural unit of formula (III)

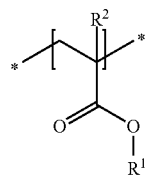 (I)

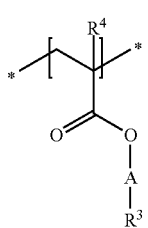 (II)

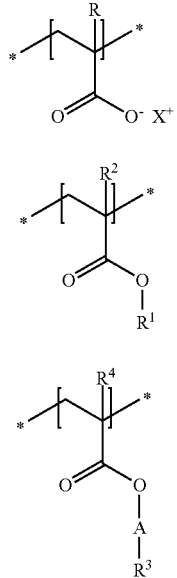 (III)

in which

R and R², independently of one another, stand for a hydrogen atom or a methyl group, R¹ stands for a $C_2$-$C_4$ alkyl chain, in particular an ethyl group, R³ stands for a saturated and linear $C_{16}$-$C_{20}$ alkyl group, R⁴ stands for a methyl group, A stands for a group *—$(CH_2CH_2O)_x$—*, in which x stands for integers from 15 to 25, and $X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom.

b) at least one uncrosslinked cationic polymer, comprising at least one structural unit of formula (IV) and at least one structural unit of formula (V) and at least one structural unit of formula (VI) and at least one structural unit of formula (VII)

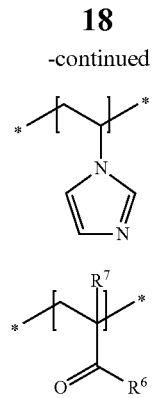 (IV)

(V)

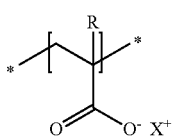 (VI)

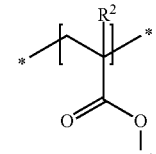 (VII)

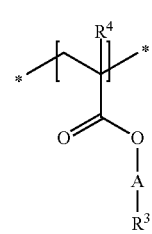

in which n stands for a methylene unit,

R⁵ stands for a methyl group,

R⁶ stands for an $NH_2$ group,

R⁷ stands for a methyl group, and $Z^-$ stands for methosulfate, and c) water in a total amount of from 80 to 98% by weight.

(B):

Cosmetic composition containing, in relation to the total weight of the cosmetic composition, a) at least one uncrosslinked anionic polymer, comprising at least one structural unit of formula (I) and at least one structural unit of formula (II) and at least one structural unit of formula (III)

(I)

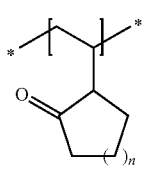

(II)

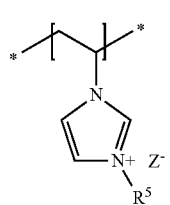

(III)

in which

R and R², independently of one another, stand for a hydrogen atom or a methyl group, R¹ stands for a $C_2$-$C_4$ alkyl chain, in particular an ethyl group, R³ stands for a saturated and linear $C_{16}$-$C_{20}$ alkyl group, R⁴ stands for a methyl group, A stands for a group *—$(CH_2CH_2O)_x$—*, in which x stands for integers from 15 to 25, and $X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom.

b) at least one uncrosslinked cationic polymer, comprising at least one structural unit of formula (IV) and at least one structural unit of formula (V) and at least one structural unit of formula (VI) and at least one structural unit of formula (VII)

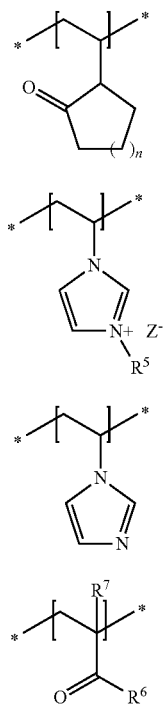

(IV)

(V)

(VI)

(VII)

in which
n stands for a methylene unit,
$R^5$ stands for a methyl group,
$R^6$ stands for an $NH_2$ group,
$R^7$ stands for a methyl group, and
$Z^-$ stands for methosulfate, and c) water in a total amount of from 80 to 98% by weight, wherein the cosmetic composition has a ratio by weight of the total amount of the at least one uncrosslinked anionic polymer a) to the total amount of the at least one uncrosslinked cationic polymer b) of from about 10:1 to about 1:30, preferentially from about 5:1 to about 1:30, preferably from about 1:1 to about 1:30, more preferably from about 1:1.5 to about 1:20, in particular from about 1:2 to about 1:15.

(C):
Cosmetic composition containing, in relation to the total weight of the cosmetic composition, a) at least one uncrosslinked anionic polymer, comprising at least one structural unit of formula (I) and at least one structural unit of formula (II) and at least one structural unit of formula (III)

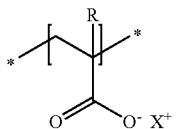

(I)

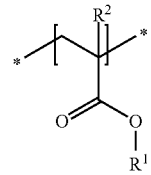

(II)

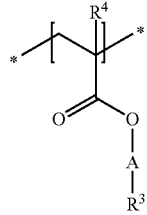

(III)

in which
R and $R^2$, independently of one another, stand for a hydrogen atom or a methyl group,
$R^1$ stands for a $C_2$-$C_4$ alkyl chain, in particular an ethyl group,
$R^3$ stands for a saturated and linear $C_{16}$-$C_{20}$ alkyl group,
$R^4$ stands for a methyl group,
A stands for a group *—$(CH_2CH_2O)_x$—*, in which x stands for integers from 15 to 25, and
$X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, b) at least one uncrosslinked cationic polymer, comprising at least one structural unit of formula (IV) and at least one structural unit of formula (V) and at least one structural unit of formula (VI) and at least one structural unit of formula (VII)

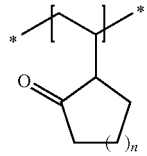

(IV)

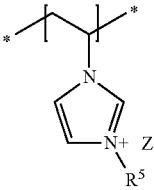

(V)

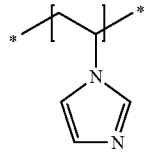

(VI)

-continued

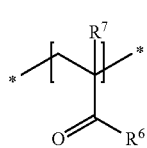
(VII)

in which
n stands for a methylene unit,
$R^5$ stands for a methyl group,
$R^6$ stands for an $NH_2$ group,
$R^7$ stands for a methyl group, and
$Z^-$ stands for methosulfate, and
c) water in a total amount of from about 80 to about 98% by weight,
wherein the cosmetic composition contains less than 0.1% by weight, preferably less than 0.05% by weight, preferably less than 0.01% by weight, in particular 0% by weight, in relation to the total weight of the cosmetic composition, of crosslinked polymers.

(D):
Cosmetic composition containing, in relation to the total weight of the cosmetic composition,
a) at least one uncrosslinked anionic polymer, comprising at least one structural unit of formula (I) and at least one structural unit of formula (II) and at least one structural unit of formula (III)

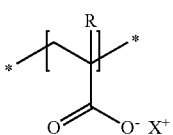
(I)

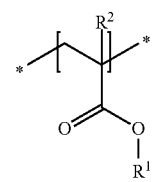
(II)

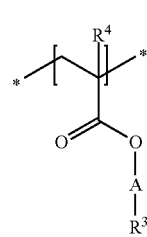
(III)

in which
R and $R^2$, independently of one another, stand for a hydrogen atom or a methyl group,
$R^1$ stands for a $C_2$-$C_4$ alkyl chain, in particular an ethyl group,
$R^3$ stands for a saturated and linear $C_{16}$-$C_{20}$ alkyl group,
$R^4$ stands for a methyl group,
A stands for a group *—$(CH_2CH_2O)_x$—*, in which x stands for integers from 15 to 25, and
$X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, b) at least one uncrosslinked cationic polymer, comprising at least one structural unit of formula (IV) and at least one structural unit of formula (V) and at least one structural unit of formula (VI) and at least one structural unit of formula (VII)

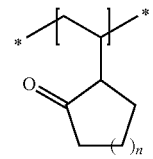
(IV)

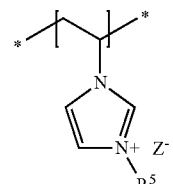
(V)

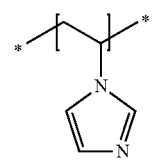
(VI)

(VII)

in which
n stands for a methylene unit,
$R^5$ stands for a methyl group,
$R^6$ stands for an $NH_2$ group,
$R^7$ stands for a methyl group, and
$Z^-$ stands for methosulfate, and
c) water in a total amount of from about 80 to about 98% by weight,
wherein the cosmetic composition additionally contains at least one film-forming and/or firming polymer, selected from copolymers of polyvinylpyrrolidone and vinyl acetate.

(E):
Cosmetic composition containing, in relation to the total weight of the cosmetic composition,
a) at least one uncrosslinked anionic polymer, comprising at least one structural unit of formula (I) and at least one structural unit of formula (II) and at least one structural unit of formula (III)

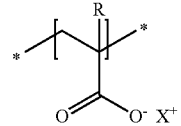
(I)

-continued

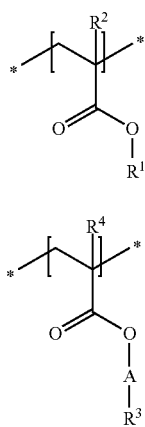

(II)

(III)

in which
R and $R^2$, independently of one another, stand for a hydrogen atom or a methyl group,
$R^1$ stands for a $C_2$-$C_4$ alkyl chain, in particular an ethyl group,
$R^3$ stands for a saturated and linear $C_{16}$-$C_{20}$ alkyl group,
$R^4$ stands for a methyl group,
A stands for a group *—$(CH_2CH_2O)_x$—*, in which x stands for integers from 15 to 25, and
$X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, b) at least one uncrosslinked cationic polymer, comprising at least one structural unit of formula (IV) and at least one structural unit of formula (V) and at least one structural unit of formula (VI) and at least one structural unit of formula (VII)

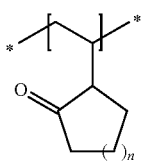

(IV)

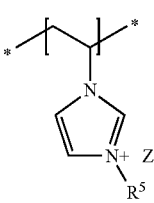

(V)

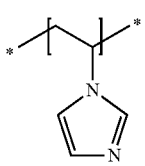

(VI)

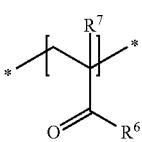

(VII)

in which
n stands for a methylene unit,
$R^5$ stands for a methyl group,
$R^6$ stands for an $NH_2$ group,
$R^7$ stands for a methyl group, and
$Z^-$ stands for methosulfate, and c) water in a total amount of from about 80 to about 98% by weight,
wherein the cosmetic composition contains at least one propellant in a total amount of from about 2.0 to about 20% by weight, preferably from about 4.0 to about 15% by weight, in particular from about 5.0 to about 10% by weight.

(F):
Cosmetic composition containing, in relation to the total weight of the cosmetic composition,
a) at least one uncrosslinked anionic polymer, comprising at least one structural unit of formula (I) and at least one structural unit of formula (II) and at least one structural unit of formula (III)

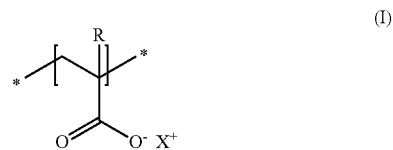

(I)

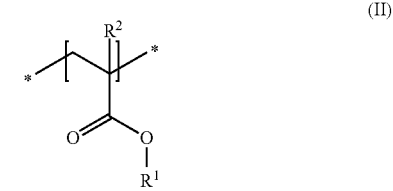

(II)

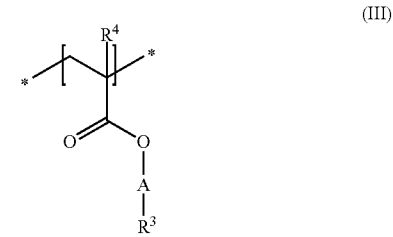

(III)

in which
R and $R^2$, independently of one another, stand for a hydrogen atom or a methyl group,
$R^1$ stands for a $C_2$-$C_4$ alkyl chain, in particular an ethyl group,
$R^3$ stands for a saturated and linear $C_{16}$-$C_{20}$ alkyl group,
$R^4$ stands for a methyl group,
A stands for a group *—$(CH_2CH_2O)_x$—*, in which x stands for integers from 15 to 25, and
$X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, in a total amount of from about 0.05 to about 2% by weight, preferably from about 0.1 to about 1.5% by weight, in particular from about 0.2 to about 1% by weight, b) at least one uncrosslinked cationic polymer, comprising at least one structural unit of formula (IV) and at least one structural unit of formula (V) and at least one structural unit of formula (VI) and at least one structural unit of formula (VII)

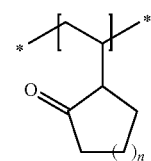
(IV)

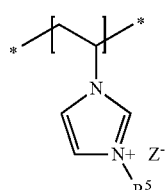
(V)

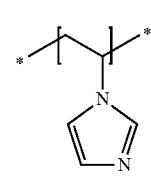
(VI)

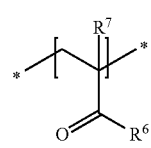
(VII)

in which
n stands for a methylene unit,
$R^5$ stands for a methyl group,
$R^6$ stands for an $NH_2$ group,
$R^7$ stands for a methyl group, and
$Z^-$ stands for methosulfate, in a total amount of from about 0.1 to about 5% by weight, preferably from about 0.2 to about 5% by weight, preferably from about 0.3 to about 3% by weight, in particular from about 0.5 to about 2% by weight, and c) water in a total amount of from about 80 to about 98% by weight.

(G):
Cosmetic composition containing, in relation to the total weight of the cosmetic composition,
a) at least one uncrosslinked anionic polymer, comprising at least one structural unit of formula (I) and at least one structural unit of formula (II) and at least one structural unit of formula (III)

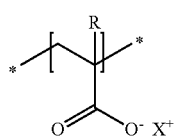
(I)

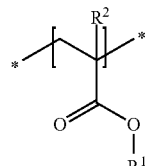
(II)

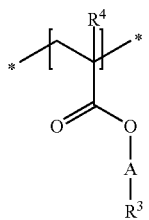
(III)

in which
R and $R^2$, independently of one another, stand for a hydrogen atom or a methyl group,
$R^1$ stands for a $C_2$-$C_4$ alkyl chain, in particular an ethyl group,
$R^3$ stands for a saturated and linear $C_{16}$-$C_{20}$ alkyl group,
$R^4$ stands for a methyl group,
A stands for a group *—$(CH_2CH_2O)_x$—*, in which x stands for integers from 15 to 25, and
$X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, in a total amount of from about 0.05 to about 2% by weight, preferably from about 0.1 to about 1.5% by weight, in particular from about 0.2 to about 1% by weight, b) at least one uncrosslinked cationic polymer, comprising at least one structural unit of formula (IV) and at least one structural unit of formula (V) and at least one structural unit of formula (VI) and at least one structural unit of formula (VII)

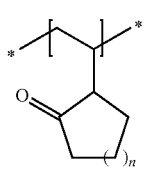
(IV)

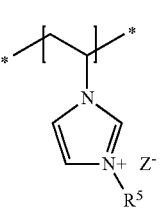
(V)

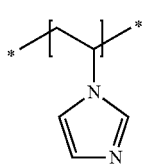
(VI)

-continued (VII)

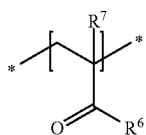

in which n stands for a methylene unit, $R^5$ stands for a methyl group, $R^6$ stands for an $NH_2$ group, $R^7$ stands for a methyl group, and $Z^-$ stands for methosulfate, in a total amount of from about 0.1 to about 5% by weight, preferably from about 0.2 to about 5% by weight, preferably from about 0.3 to about 3% by weight, in particular from about 0.5 to about 2% by weight, and c) water in a total amount of from about 80 to about 98% by weight, wherein the cosmetic composition contains less than 0.1% by weight, preferably less than 0.05% by weight, preferably less than 0.01% by weight, in particular 0% by weight, in relation to the total weight of the cosmetic composition, of cross-linked polymers.

(H):

Cosmetic composition containing, in relation to the total weight of the cosmetic composition, a) at least one uncrosslinked anionic polymer, comprising at least one structural unit of formula (Ia) and at least one structural unit of formula (Ib) and at least one structural unit of formula (IIa) and at least one structural unit of formula (IIb) and at least one structural unit of formula (III)

(Ia)

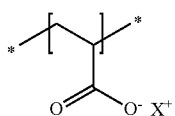

(Ib)

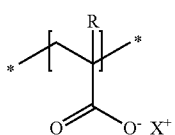

(IIa)

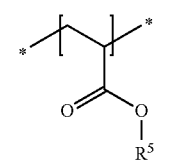

(IIb)

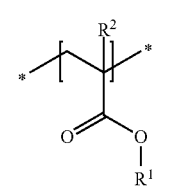

(III)

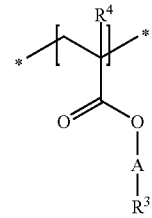

in which

R, $R^2$ and $R^4$, independently of one another, stand for a methyl group, $R^1$ and $R^5$, independently of one another, stand for a $C_2$-$C_4$ alkyl chain, in particular an ethyl group, $R^3$ stands for a saturated and linear $C_{16}$-$C_{20}$ alkyl group, $R^4$ stands for a methyl group, A stands for a group *—$(CH_2CH_2O)_x$—*, in which x stands for integers from 15 to 25, and $X^+$ stands for metal cations of the physiologically acceptable metals from the groups Ia, Ib, IIa, IIb, IIIb, VIa or VIII of the Periodic Table of Elements, ammonium ions, and also cationic organic compounds with quaternized nitrogen atom, b) at least one uncrosslinked cationic polymer, comprising at least one structural unit of formula (IV) and at least one structural unit of formula (V) and at least one structural unit of formula (VI) and at least one structural unit of formula (VII)

(IV)

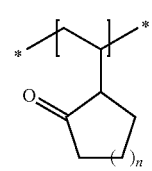

(V)

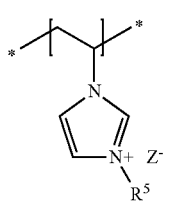

(VI)

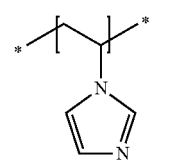

(VII)

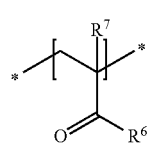

in which n stands for a methylene unit, $R^5$ stands for a methyl group, $R^6$ stands for an $NH_2$ group, $R^7$ stands for a methyl group, and $Z^-$ stands for methosulfate, and c) water in a total amount of from about 80 to about 98% by weight, The aforementioned particularly preferred embodiments (A) to (H) of the cosmetic compositions as contemplated herein are characterized by excellent sprayability in spite of their gel-like consistency or high viscosity, and result, after application to keratinic fibers, in particular human hair, in an excellent prolonged hold and also in a high volume effect of the keratinic fibers treated with these cosmetic compositions.

The cosmetic composition as contemplated herein is preferably provided as a product that can be sprayed. A further subject of the present disclosure is therefore a cosmetic product comprising
a) a dispensing device with spray valve,
b) a cosmetic composition as contemplated herein disposed in the dispensing device, and
c) propellant in a total amount of from 0 to 95% by weight, in relation to the total weight of the cosmetic composition disposed in the dispensing device.

In accordance with a preferred embodiment of this subject, the dispensing device is an aerosol or a non-aerosol container. An aerosol container is understood within the scope of the disclosure to mean a compressed gas container filled with propellant, with the aid of which the cosmetic composition as contemplated herein disposed inside the aerosol container is distributed by the inner gas pressure of the aerosol container via a valve. By contrast, a non-aerosol container is understood in accordance with the disclosure to mean a container under normal pressure, with the aid of which the cosmetic composition as contemplated herein disposed inside the non-aerosol container is distributed as a spray mist by mechanical action, in particular by a pumping or squeezing system.

The cosmetic product as contemplated herein, which is present in the form of an aerosol spray, can be produced in the usual way. All constituents of the cosmetic composition as contemplated herein are generally filled into a suitable pressure-resistant container. This is then closed using a valve. The desired amount of the specific propellant is lastly filled via conventional techniques.

Vessels made of metal (aluminum, tinplate, tin), protected plastic or non-splintering plastic, or glass coated externally with plastic are potential pressure-resistant containers, wherein the compressive strength, breaking strength, corrosion resistance, ease of filling and also aesthetic considerations, ease of handling, printability, etc. play a role when selecting such a vessel. Special internal protective coatings ensure resistance to corrosion in respect of the cosmetic composition as contemplated herein disposed in the pressure container. The used valves particularly preferably have an internally coated valve disk, wherein the coating and valve material are compatible with one another. If aluminum valves are used, the valve disks thereof can be coated internally, for example with Micoflex. If tinplate valves are used in accordance with the disclosure, the valve disks thereof can be coated internally for example with PET (polyethylene terephthalate). With a given spraying device, the sizes of the aerosol droplets and the size distribution can be adjusted via the ratio of propellant to the other constituents of the preparations.

The spraying rate of the aerosol spray as contemplated herein is preferably about 6.5 to about 10.0 g/10 s.

Particularly preferred cosmetic products as contemplated herein in the form of an aerosol spray are provided in an aerosol container having a stem valve with a stem bore having a diameter from about 0.27 to about 0.35 mm. Such valves are sold for example as valves of the KE type or of the KEN type by the company Coster.

The cosmetic compositions as contemplated herein, however, can also be packaged in a multi-chamber dispenser. The multi-chamber dispenser can be used such that one chamber is filled with the compressed propellant and another chamber is filled with the rest of the constituents of the cosmetic composition as contemplated herein. A multi-chamber dispenser of this type is what is known as a "bag-in-can" packaging form, for example.

The cosmetic compositions as contemplated herein in the form of non-aerosols or spray mist preparations can be extracted in any arbitrary propellant-gas-free spraying system comprising a dispensing container and a spray valve, i.e. for example in a flexible pressure cylinder with immersion tube and spray valve (squeeze bottle), in a balloon nebulizer, which works in accordance with the Venturi principle, or in a pump-spray cylinder, the pump handle of which is actuated using the index finger or using the whole hand in the manner of a trigger. In an embodiment of the cosmetic product in the form of a non-aerosol preferred for the cosmetic application, the dispensing container has a manually actuated spray pump.

With regard to further preferred embodiments of the cosmetic product as contemplated herein, that which has been stated with regard to the cosmetic compositions applies, mutatis mutandis.

In addition, a further subject of the present disclosure is a method for temporarily deforming keratinic fibers, wherein the method comprises the following method steps:
a) providing a cosmetic composition as contemplated herein or a cosmetic product as contemplated herein,
b) applying, in particular, spraying, the cosmetic composition as contemplated herein or the cosmetic product as contemplated herein onto the keratinic fibers,
c) distributing the applied, in particular sprayed-on, cosmetic composition as contemplated herein or the cosmetic product as contemplated herein over the keratinic fibers and deforming the keratinic fibers into the desired form.

Within the scope of the method as contemplated herein, provision can be made so that the deformation of the keratinic fibers in method step c) is carried out at ambient temperature and/or at a temperature of at least 40° C., in particular of at least 50° C. The term "ambient temperature" is understood here to mean the temperature which is present without use of heating sources, such as hairdryers, straightening irons, or heat hoods, or cooling sources. If the deformation of the keratinic fibers, in particular human hair, is to be carried out at higher temperatures of at least 40° C., it is preferred in accordance with the disclosure when the deformation is carried out with use of a hairdryer, a straightening iron, a heat hood, etc. In this case, the keratinic fibers can be heated during the deformation. However, it can also be provided to heat the keratinic fibers after the application and/or after the distribution of the cosmetic composition as contemplated herein.

With regard to further preferred embodiments of the method as contemplated herein, that which has been stated in respect of the cosmetic compositions as contemplated herein and also in respect of the cosmetic product as contemplated herein applies, mutatis mutandis.

Lastly, a further subject of the present disclosure is the use of a cosmetic product as contemplated herein or of a cosmetic product as contemplated herein for temporarily deforming keratinic fibers.

With regard to further preferred embodiments of the use as contemplated herein, that which has been stated in respect of the cosmetic compositions as contemplated herein, in respect of the cosmetic product as contemplated herein, and in respect of the method as contemplated herein applies, mutatis mutandis.

The following examples explain the present disclosure, but are not intended to be limiting:

EXAMPLES

1. Formulations (all values are in % by weight and relate to the total weight of the corresponding cosmetic composition):

| Raw material | V1 | E1** | E2** | E3** | E4** |
|---|---|---|---|---|---|
| Aculyn 22[1)] | — | 0.60* | 0.60* | 0.30* | 1.0* |
| Carbomer | 0.60* | — | — | — | — |
| Luviquat Supreme AT[2)] | — | 1.0* | 1.0* | 1.5* | 0.8* |
| PVP/VA Copolymer 60:40 | 1.0* | — | 1.0* | — | — |
| 2-amino-2-methyl-1-propanol | 0.19 | 0.19 | 0.19 | 0.095 | 0.32 |
| PEG-12 dimethicone | 0.32 | 0.32 | — | 0.80 | 0.50 |
| PEG-14 dimethicone | 1.0 | 1.0 | 1.5 | — | 0.70 |
| PEG-40 hydrogenated castor oil | 0.30 | 0.30 | 0.50 | 0.20 | 0.40 |
| Fragrance | 0.15 | 0.15 | 0.15 | 0.15 | 0.15 |
| Water | to 100 | to 100 | to 100 | to 100 | to 100 |

*active substance content
**as contemplated herein
[1)]INCI name: Acrylates/Steareth-20 Methacrylate Copolymer (29.5-30.5% dispersion in water, Rohm & Haas)
[2)]INCI name: Polyquaternium-68 (19-21% dispersion in water, BASF)

The cosmetic compositions V1 and E1 to E4 were obtained by mixing the above ingredients and were provided in the form of a gel or had a gel-like consistency. Each composition V1 and E1 to E4 was filled into an aerosol container and a non-aerosol container. In the case of aerosol products, the aerosol containers were mixed with a propellant mixture formed of propane:butane (85:15).

The contained aerosol sprays and non-aerosol sprays were then applied to keratinic fibers. All products had good spraying properties in spite of the gel-like consistency and did not result in a blocking of the spray valves. The aerosol and non-aerosol products E1 to E4, however, demonstrated a greater prolonged hold and an improved volume effect compared to the aerosol and non-aerosol product V1.

The improved volume effect of the composition E1 in comparison to the composition V1 was determined as follows:

Artificial scalps with hair were first produced by inserting individual strands of hair (Kerling International, Backnang—Germany, European Natural Hair 7/0, batch # 2013, length: 8 cm, width: 1 cm, weight: 2.3 g) in a curved plastic support. These scalps were then cleaned in water for 30 minutes using a solution of sodium laureth sulfate (3% by weight of active substance, pH 6-7), washed, and combed under running water for 5 minutes. After drying overnight at 50% relative atmospheric humidity and at 21° C., images of the surface of the hair parting region were then recorded using a camera in black-and-white mode (exposure time 54 ms). The scalps were moistened with water for 5 minutes and then pressed between a towel weighted down with a 2 kg weight so as to remove excess water. 5 scalps were used for each of the compositions E1 and V1. After application of 1 ml of the corresponding composition and uniform distribution to the scalps, the scalps were oriented such that the hair pointed downwardly and was dried at 40° C. for 7 minutes. The hair was then combed 2× using a brush (Braun Satin Hair 7 Deionizing Brush), was dried for a further 7 minutes, and was then cooled for 5 minutes. Black-and-white photos of the surface of the hair parting region were then taken once again (volume change 0 minutes). After storage of the scalps for 48 h at 50% relative atmospheric humidity and 21° C., the surface of the hair parting region was determined again (volume change 48 h).

Before the images were evaluated, the camera was calibrated using a black disk of known area, and a morphological filter was used in order to fill the empty areas of the hair area.

The threshold for the detection region was set at 200, and the exposure time was 54 ms.

The change to the hair volume is directly proportional to the change in area and can be determined by means of the following formula:

volume change $[\%] = (\text{area}_{treated} - \text{area}_{untreated})/(\text{area}_{untreated}) * 100$ The obtained volume changes were examined by means of statistical methods (Shapiro-Wilks test, Bartlett test, Newman-Keuls test) and were statistically significant.

| Composition | Volume change 0 minutes | volume change 48 h |
|---|---|---|
| V1 | 141 | 37 |
| E1* | 223 | 160 |

*as contemplated herein

The use as contemplated herein of a combination of a specific uncrosslinked anionic polymer and a specific uncrosslinked cationic polymer leads to a significantly improved hair volume following application of the cosmetic compositions as contemplated herein.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

The invention claimed is:

1. A cosmetic composition for temporarily deforming keratinic fibers, consisting of:
   about 0.05 to about 2% by weight of acrylates/steareth-20 methacrylate copolymer;
   about 0.1 to about 5% by weight of polyquaternium-68;
   2-amino-2-methyl- 1-propanol;
   PEG-12 dimethicone;
   PEG-14 dimethicone;
   PEG-40 hydrogenated castor oil;
   fragrance; and
   water.

2. The cosmetic composition according to claim 1, wherein the acrylates/steareth-20 methacrylate copolymer is from about 0.1 to about 1.5% by weight in relation to the total weight of the cosmetic composition.

3. The cosmetic composition according to claim 1, wherein the acrylates/steareth-20 methacrylate copolymer is from about 0.2 to about 1% by weight in relation to the total weight of the cosmetic composition.

4. The cosmetic composition according to claim 1, wherein the polyquaternium-68 is from about 0.3 to about 3% by weight in relation to the total weight of the cosmetic composition.

5. The cosmetic composition according to claim 1, wherein the polyquaternium-68 is from about 0.2 to about 5% by weight in relation to the total weight of the cosmetic composition.

* * * * *